(12) United States Patent
Kurz (10) Patent No.: US 11,624,907 B2
(45) Date of Patent: Apr. 11, 2023

(54) METHOD AND DEVICE FOR EYE METRIC ACQUISITION

(71) Applicant: HEADS STOCKHOLM AB, Stockholm (SE)

(72) Inventor: Hans-Peter Kurz, Stockholm (SE)

(73) Assignee: HEADS STOCKHOLM AB

( * ) Notice: Subject to any disclaimer, the term of this patent is extended or adjusted under 35 U.S.C. 154(b) by 0 days.

(21) Appl. No.: 16/349,682

(22) PCT Filed: Nov. 3, 2017

(86) PCT No.: PCT/SE2017/051098
§ 371 (c)(1),
(2) Date: May 14, 2019

(87) PCT Pub. No.: WO2018/093313
PCT Pub. Date: May 24, 2018

(65) Prior Publication Data
US 2019/0361231 A1    Nov. 28, 2019

(30) Foreign Application Priority Data
Nov. 15, 2016    (SE) .................................... 1651488-7

(51) Int. Cl.
*G02B 27/00*    (2006.01)
*G06F 3/01*    (2006.01)
(Continued)

(52) U.S. Cl.
CPC ......... *G02B 27/0093* (2013.01); *G06F 3/013* (2013.01); *G06V 10/147* (2022.01);
(Continued)

(58) Field of Classification Search
CPC ............... G02B 27/0093; G06K 9/209; G06K 9/00221; G06K 9/00604; G06F 3/013;
(Continued)

(56) References Cited

U.S. PATENT DOCUMENTS 8,824,779 B1 *  9/2014  Smyth .................... G06T 7/593
                                                    382/154
8,885,882 B1    11/2014  Yin et al.
(Continued)

FOREIGN PATENT DOCUMENTS

EP    1 452 127 A1    9/2004
EP    1 829 479 A1    9/2007
(Continued)

OTHER PUBLICATIONS

Notice of Reasons for Refusal Japanese Patent Application No. 2019-524069, dated Jun. 10, 2021, 3 pages.

*Primary Examiner* — Umair Ahsan
(74) *Attorney, Agent, or Firm* — Condo Roccia Koptiw LLP (57) ABSTRACT

The present disclosure relates to a method and a device for acquisition of a metric of an eye (1) located in an acquisition space (29). The device comprises at least one light source (11) configured to emit light towards the acquisition space, a camera (15) configured to receive light from the acquisition space to (29) generate image data, and an analyzing unit (14) configured to extract at least one metric from the image data. The camera (15) is configured to receive light from the acquisition space via at least two light paths (17, 19) which are differently angled with respect to the optical axis of the camera, the light of at least one path being received via a first mirror (21). The camera receives light from an overlapping portion of the acquisition space via the first and second paths, as to allow the camera to receive at least two representations of a single eye. This metric may be used for e.g. eye tracking or autorefraction/accomodation.

16 Claims, 5 Drawing Sheets

(51) Int. Cl.
*G06V 10/147* (2022.01)
*G06V 40/16* (2022.01)
*G06V 40/19* (2022.01)
*A61B 3/00* (2006.01)
*A61B 17/00* (2006.01)

(52) U.S. Cl.
CPC .............. *G06V 40/16* (2022.01); *G06V 40/19* (2022.01); *A61B 3/0008* (2013.01); *A61B 2017/00216* (2013.01); *G05B 2219/35503* (2013.01)

(58) Field of Classification Search
CPC ........ A61B 2017/00216; A61B 3/0008; G05B 2219/35503
See application file for complete search history.

(56) References Cited

U.S. PATENT DOCUMENTS

| | | | |
|---|---|---|---|
| 2003/0223037 A1* | 12/2003 | Chernyak | A61F 9/00806 351/209 |
| 2007/0116331 A1 | 5/2007 | Rowe et al. | |
| 2013/0089236 A1* | 4/2013 | Malhas | G06K 9/00604 382/103 |
| 2014/0098198 A1 | 4/2014 | Lee et al. | |
| 2015/0185503 A1* | 7/2015 | Tate | G02C 7/083 351/158 |
| 2016/0080720 A1 | 3/2016 | Fullam | |
| 2016/0180591 A1* | 6/2016 | Shiu | G06F 3/013 345/633 |
| 2019/0041634 A1* | 2/2019 | Popovich | G02B 27/017 |

FOREIGN PATENT DOCUMENTS

| | | |
|---|---|---|
| EP | 2 696 259 A1 | 2/2014 |
| JP | H11235316 A | 8/1999 |
| KR | 20140045873 A | 4/2014 |

* cited by examiner

METHOD AND DEVICE FOR EYE METRIC ACQUISITION

CROSS REFERENCE TO RELATED APPLICATIONS

This application is the National Stage Entry under 35 U.S.C. § 371 of Patent Cooperation Treaty Application No. PCT/SE2017/051098, filed Nov. 3, 2017, which claims priority from Sweden Application No. 1651488-7, filed Nov. 15, 2016, the contents of which are hereby incorporated by reference herein.

FIELD OF THE INVENTION

The present disclosure relates to a device for acquisition of an eye metric of an eye located in an acquisition space. The device comprises at least one light source configured to emit light towards the acquisition space, a camera configured to receive light from the acquisition space to generate image data, and an analysing unit configured to extract at least one metric from the image data.

The present disclosure also relates to a corresponding method.

BACKGROUND OF THE INVENTION

Such a device is disclosed for instance in EP-2696259-A1, and may be used as an input device, allowing a user to control for instance a computer using his eyes, or to carry out behavioural studies, testing how a person react to different stimuli, etc. A general problem with such systems is how to make them more efficient and robust, for instance to deal with optical disturbances of various kinds.

SUMMARY OF THE INVENTION

One object of the present disclosure is therefore to provide an eye metric acquisition device which is capable of robust metric acquisition.

This object is achieved by means of a device as defined in claim 1. More specifically, in a device of the initially mentioned kind, the camera is configured to receive light from the acquisition space via at least first and second light paths, at different angles with respect to the optical axis of the camera. Light of at least the first light path is received via a first mirror, and in such a way that the camera receives light from an overlapping portion of the acquisition space via the first and second paths. Therefore, the camera receives at least two representations of a single eye.

This means that in one single image, two representations of the eye can be generated, and as seen from slightly different directions. Even if one representation, in the form of a first sub-image, is distorted, for instance due to a large gaze angle or the user's glasses, the other representation, in the form of a second sub-image can provide information useful for eye metric acquisition. This provides a more robust metric acquisition.

Typically, the light of the second light path may be received via a second mirror. Further, the first and second light paths may have a length difference exceeding 1 of the shortest length. This means that the probability becomes greater that one of images produced is within the focus depth of the camera. Therefore, a smaller focus depth can be allowed, for instance using a larger camera aperture, which allows faster image capturing.

The camera may be configured to receive light from a plurality of mirrors, each providing a separate light path between the acquisition space and the camera which pictures an area of the acquisition space that overlaps with the area of another mirror. This provides very robust capturing. The plurality of mirrors may be disposed on a concave surface facing the acquisition space. The angle between a mirror normal vector and the camera's optical axis may be less than 15° which allows the mirror to present a relatively flat image to the camera.

The analyzing unit may be configured to determine a glint to pupil distance to determine a user's eye optical axis, i.e. gaze angle. This allows the produced data to be used for eye tracking.

The analyzing unit may also be configured to determine a user's eye gaze angle by carrying out an analysis based on at least two representations of a single eye. This may allow a gaze angle to be determined even without producing a glint in the eye's cornea.

Alternatively, or in combination therewith, the analyzing unit may be configured to record images of user's retina to determine an eye's refractive error, or may be configured to determine an iris angular feature to determine a user's eye optical torsion.

A dichroic filter mirror may be located between the acquisition space and the first mirror. This allows the system to display stimuli to the eyes in the visible spectrum, while e.g. carrying out eye tracking in the infrared spectrum. More than one such dichroic mirror may be used, such that different content can be displayed e.g. to the right and left eye, for instance allowing 3D effects.

The light source may typically produce light in the infrared spectrum.

A corresponding method is also considered.

DETAILED DESCRIPTION OF THE EXEMPLARY EMBODIMENTS

The present disclosure relates in general to devices and methods for acquisition of an eye metric. Such acquisition may be accomplished by emitting light, by means of a light source towards an eye, capturing an image of the eye to provide image data, and an analyzing the data to extract at least one metric therefrom. Exemplary applications where such eye metric acquisition takes place is eye tracking and autorefraction.

By eye tracking is meant the measuring of a gaze vector, i.e. the direction in which an eye is looking, or the motion of an eye relative to the head. Eye trackers may be used for instance in behavioral studies, e.g. to determine how a person reacts to certain stimuli, or as an input devide, allowing a user to control a computer using eye movements. Eye movements take place as a series of saccades. By a saccade is meant the quick eye movement between two successive fixations of the eye. A human saccade take often last between 20 and 100 ms, and can reach a velocity of up to 800° per second. A number of subsequent detected gaze vectors describe how the eye moves.

Figure 1:
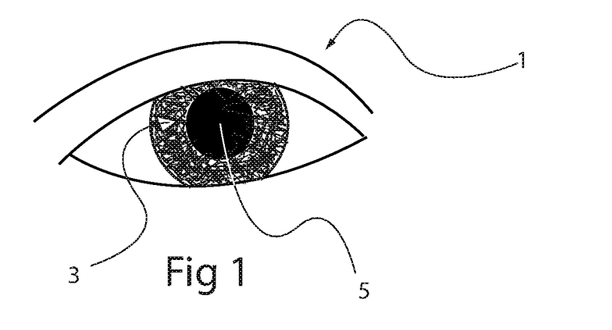
FIG. 1 illustrates an image captured of an eye which is lit from the side.

Typically, a light source may be arranged at the side of the eye. In a resulting image of an eye 1, as illustrated in FIG. 1, there is produced a visible glint 3 on the cornea thereof. By measuring the relative positions of the glint 3 and the centre of the eye's pupil 5, a measure of the eye's gaze vector may be obtained.

With the present eye metric acquisition device it is also possible to detect a gaze angle without the use of a glint as will be discussed further.

In the following, the terms hot and cold mirrors are used. By a cold mirror is meant a mirror comprising a dichroic filter, such that the mirror reflects the visible light spectrum while efficiently transmitting longer (typically higher than 700 nm) infrared wavelengths. Hot mirrors function in the opposite manner, transmitting the visible spectrum while reflecting infrared light. Hot and cold mirrors are well known per se.

A known eye tracking arrangement can be devised e.g. as a remote or a mobile eye tracker. A remote tracker captures images of eyes from a fixed location at a distance from the acquisition space where the eyes reside. Mobile trackers on the other hand can be mounted on the user's head, to automatically compensate for any head movements, or can be arranged to follow the user's eyes dynamically in other ways. By the user is here meant the person whose eye metrics are acquired.

An eye tracker can be provided with a chin rest to ensure that the user's head moves only very little, and that the eyes therefore are confined to a very small acquisition space. This allows higher camera framerates to be used, over 500 Hz at the expense of the user being immobilized. Alternatively, the camera is devised to allow a greater acquisition space, e.g. an imaginary box sized 40×30×25 cm allowing the user to move his head. This however limits the framerate as it is difficult to read out an image with high resolution at high pace.

Users with glasses may cause problems as one or several additional glints or reflections can be read out, one in the cornea and unwanted reflections by the glasses at the side thereof. It may be difficult for the analysing unit to determine which glint is to be used for gaze vector detection. This problem may be particularly pronounced when the glasses are strong, e.g. −6 diopters and att large gaze angles. It is even possible that an additional pupil is detected for each eye, one seen through the glasses and the same pupil again seen directly next to the glasses, thus further complicating the analyzing. The present disclosure seeks to at least partially reduce one or more of the aforementioned difficulties.

Typically, eye tracking can be carried out within the infrared part of the electromagnetic spectrum. This reduces image processing requirements, only having to process a limited spectrum, and allows the visible part of the spectrum to be used e.g. to provide stimuli to the user. For instance, using a cold mirror a visible image can be shown to the user by reflecting an image perpendicularly from the optical axis of the user's eyes while the infrared wavelengths are used to detect eye movements in the elongation of the optical axis behind the cold mirror. In such a case, the user does not see the tracking arrangement.

Figure 2:
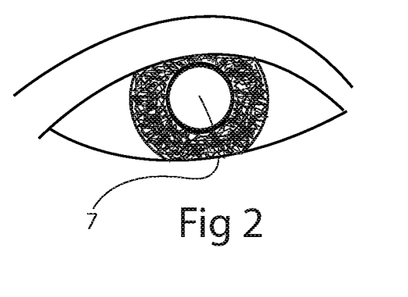
FIG. 2 illustrates an image captured of an eye which is lit from a location close to its optical axis.

By autorefraction is meant an arrangment for assessing refractive errors of a user's eyes. Typically images are captured of a user's eye as seen from close to the eye's optical axis. Light sources are lit sequentially from locations slightly displaced from the optical axis at different angles. This means that a camera can capture a set of images of the eye's retina, so called bright pupil 7 images, as shown in FIG. 2. By comparing a number of these images, a measure of refractive errors, spherical and/or cylindrical, can be obtained. In per se known example, a camera can be located at about 1 meter distance from the eye with six light sources located around the camera, evenly spaced apart around a circle having the optical axis of the camera in its centre. In other embodiments, a camera can be located much closer to the eye. A number of repetetive autrefraction measurements can provide an accomodation metric.

Figure 3:
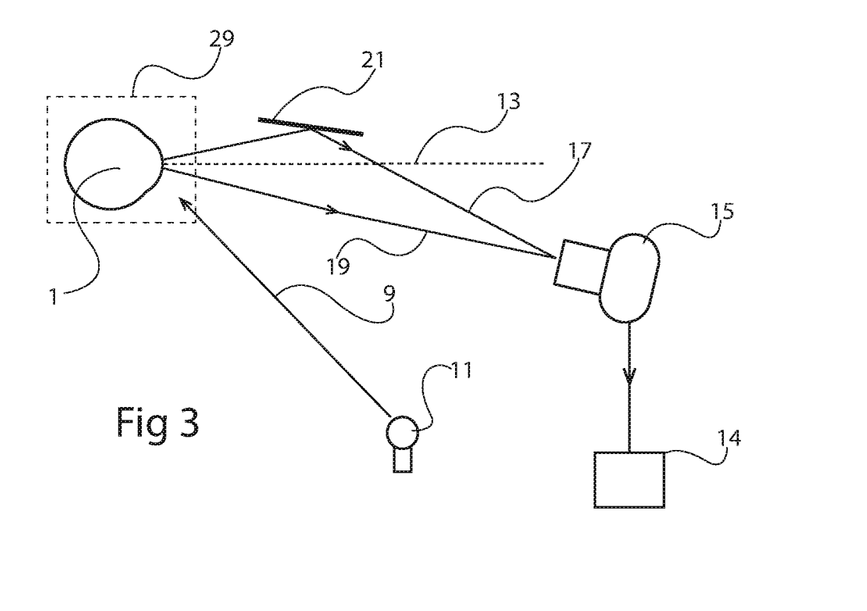
FIG. 3 schematically illustrates an arrangement for acquisition of an eye metric.

FIG. 3 schematically illustrates, in a simple form, an arrangement for acquisition of an eye metric according to the present disclosure. Light is emitted in a beam 9 from a light source 11 towards an eye 1. If this light source 11 is located distant from the optical axis 13 of the eye 1, a glint 3 will be visible as previously shown in FIG. 1. A camera 15 captures an image of the eye 1. The camera 15 receives light from the acquisition space 29, where the eye is located, via a first 17 and a second 19 light path. The first and second paths 17, 19 are differently angled with respect to the optical axis of the camera and with respect to the optical axis 13 of the eye. This is achieved by means of a mirror 21 which is arranged to accomplish the first light path. The camera 15 thus receives light from overlapping portions of the eye, providing at least two representations therof.

The angular setup of FIG. 3 will of course receive a relatively distorted image via the mirror, and while this may be perfectly useful and the distortion may be compensated for by means of image analysis software, other setups may be more useful in some situations.

Figure 4:
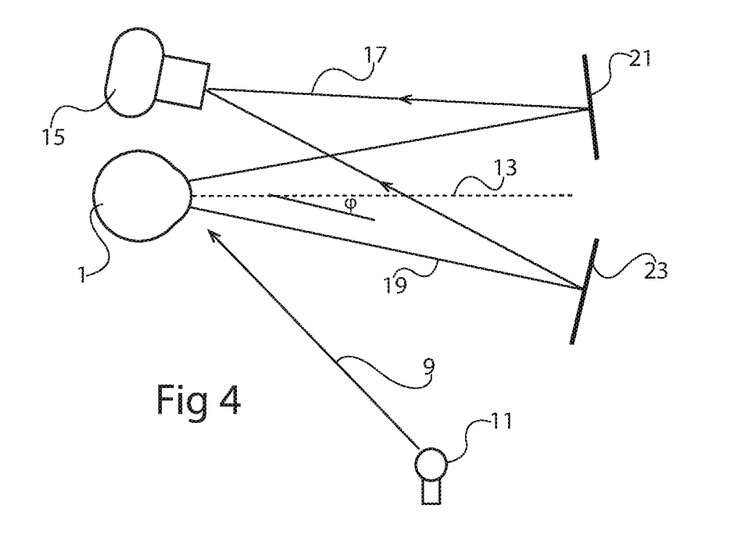
FIG. 4 schematically illustrates an arrangement suitable for eye tracking.

FIG. 4 illustrates schematically a setup useful for eye tracking applications. In this setup, the light of the second light path 19 is received via a second mirror 23. Thanks to the similar properties of the two light paths 17, 19, the two representations obtained will have relatively similar properties. As this setup does not require direct line of sight between the camera 15 and the eye 1, the optical axes of the camera and the eye can have similar directions. Further, the flat mirror 21, 23 surfaces can face the eye 1, i.e. the normal vectors of the mirrors can have an angle φ lower than 15° vis-á-vis the optical axis of the eye 1 and/or that of the camera 15. In FIG. 4, this is angle is indicated for mirror 23 and with respect to the optical axis 13 of the eye. This means that comparatively flat projections of the eye are obtained as compared to the projection obtained through the mirror 21 of FIG. 3. The mirrors 21, 23 may be hot mirrors which means that the user can watch items behind the mirrors. It is thus possible to make the mirrors only slightly visible to the user. It should be noted that the drawings of FIGS. 3-5 are schematical for illustration purposes in such a way that the geometry is not necessarily accurate.

Figure 5:
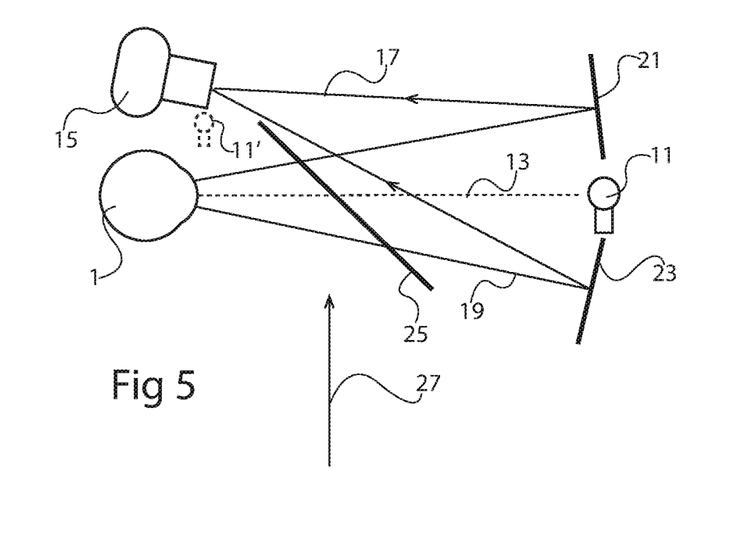
FIG. 5 schematically illustrates an arrangement suitable for autorefraction applications.

FIG. 5 illustrates an alternative where the light source 11 has been placed in close proximity to the mirrors 21,23 or close to the camera 15. When the angle between the camera and the light source as seen from the eye, through the mirrors or directly, is less than 6°, the pupil may become a bright pupil due to reflected light on the retina (cf. FIG. 2). Since the eye is captured from known angles with known geometry, the exact position of the eye and the pupil size may be known. The differences between those retina images could be used to determine a refractive error of the eye 1, i.e. autorefraction. It may be preferred to instead arrange the light source 11' together with the camera 15, as indicated in the drawing.

Bright pupil images may also be used for eye tracking purposes.

In FIG. 5 a cold mirror 25 is located in between the eye 1 on the one hand and the mirrors 21, 23 and the light source 11 on the other. This mirror may be angled about 45° with respect to the optical axis 13 of the eye such that visible light can be introduced into the eye's field of view from the side of the image capturing arrangement. This mirror does not affect the light source 11 or the capturing of images with the camera 15 and the mirrors 21, 23 as long as infrared light is used for those functions. At the same time visual spectrum stimuli 27 can be provided to the eye 1 via the cold mirror 25, such as a displayed image, flashing lights, etc. Such cold mirrors could be used also for the setup in FIG. 4. It is possible to use one single cold mirror projecting visible light towards both eyes of a user. Alternatively a separate cold mirror could be used for each eye which allows even to render 3D content to the user.

Figure 6:
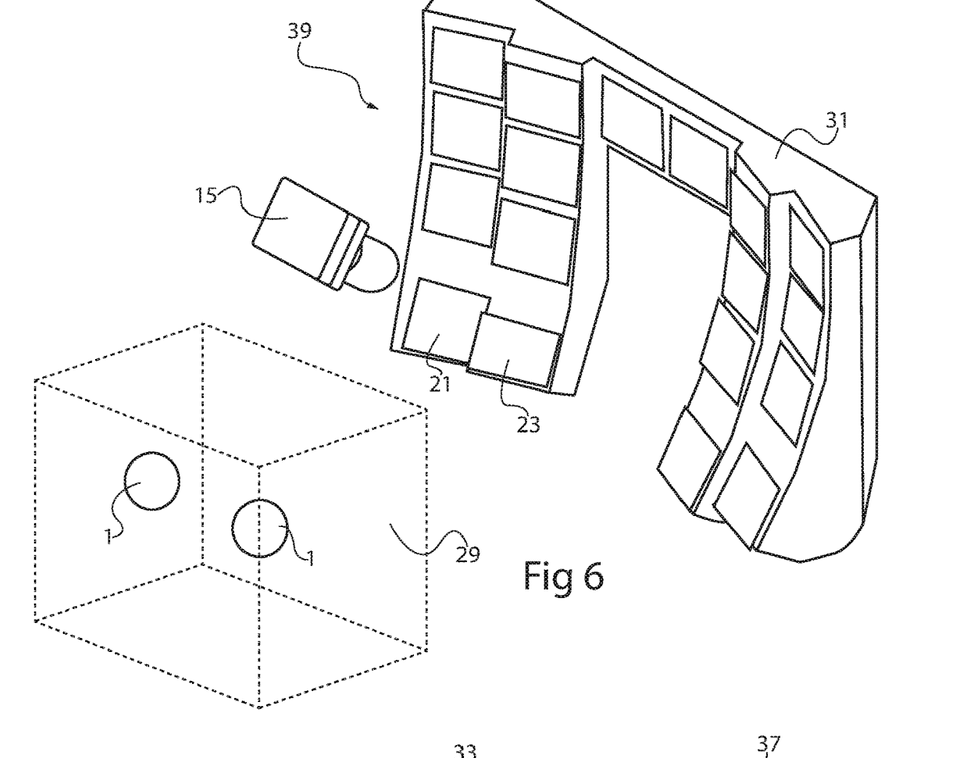
FIG. 6 shows a perspective view of an image acquisition arrangement.

FIG. 6 illustrates in perspective a setup that can be used e.g. for eye tracking. In this case, the camera 15 is located over an acquisition space 29 where the user's eyes 1 are located, and the camera faces in the same direction as does the user. A plurality of mirrors 21, 23, in the illustrated case 18 mirrors, are arranged on a mirror support 31. The faces of the mirrors are directed such that they will picture overlapping portions of the acquisition space 29. That is, the flat mirror surfaces have differently directed normal vectors. Typically, the mirrors 21, 23 are arranged over a spherical surface, such that they provide light paths with similar lengths between the camera 15 and the acquisition space 29, although those lengths may be varied as will be shown. Different overlapping schemes are possible. For instance, a pair of mirrors with a first and a second mirror may picture overlapping portions of an acquisition space as well as a pair with the second mirror and a third mirror. At the same time the first and the third mirrors need not picture overlapping portions. It is possible that two mirrors provide almost fully overlapping pictures. Due to the differently directed mirror normal vectors, the amount of overlap is also depending on how far from the mirrors the face of the user is located in the acquisition space.

Figure 7:
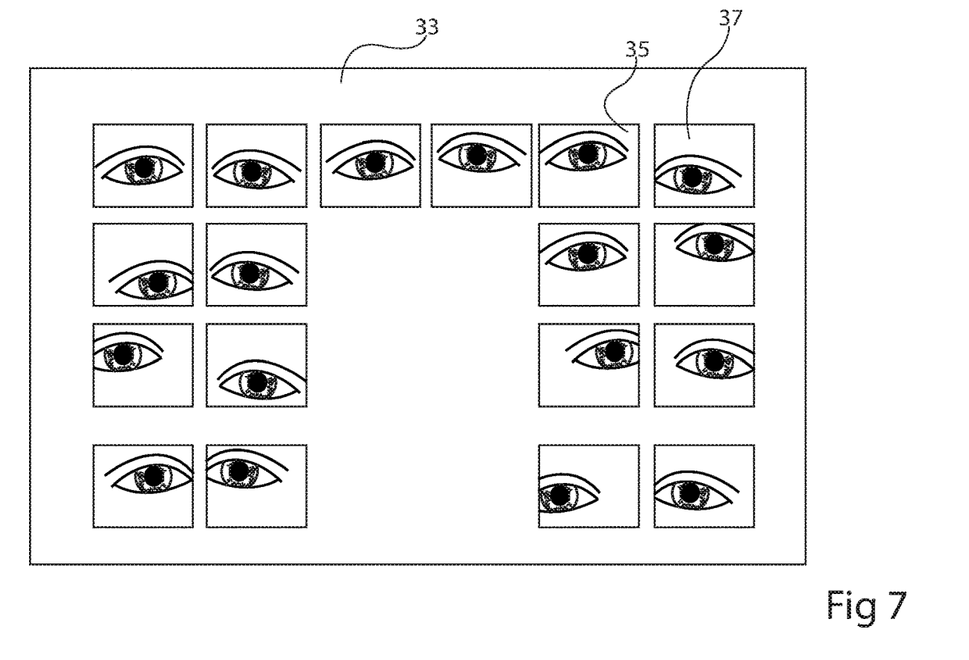
FIG. 7 illustrates an example of an image generated with the setup of FIG. 6.

FIG. 7 illustrates an image 33 captured with a setup as shown in FIG. 6. Thanks to the plurality of mirrors, a number of subimages 35, 37, representing parts of the acquisition space will be present in the image 33. Even if some of the subimages cannot be used, due to large gaze angles, glasses, etc. as metioned previously, other subimages can provide the needed information. That is to say, the geometric setup for instance as shown in FIG. 6 will in most cases provide useful content, even if the user moves or turns his head slightly, gazes sideways or up/down, or has high diopter glasses, for instance.

Additionally, some of the mirrors will most likely provide subimages depicting the eye almost straight into the pupil, which makes optional pupil size detection much simpler. Also, an iris angular feature can be detected. Irises have unique detectable patterns, and these patterns can be used to determine a user's eye optical torsion, i.e. it can be detected that the eye turns somewhat around its own optical axis.

Further, it is possible, using image data as shown in FIG. 7, to determine a gaze angle even without the use of a glint in the cornea as in FIG. 1. With image data corresponding to FIG. 7, an analyzing unit can carry out an analysis based on two or more representations of a single eye. The analyzing unit may have knowledge allowing relating a sub-portion of the image data to a specific mirror, and may further have knowledge regarding that mirror's location and inclination relative to the camera 15. It is possible to use an image analysis algorithm that, based e.g. on the location of the pupil or the iris in relation to the remainder of the eye such as eyelids, etc., to determine the gaze angle of the eye. This may for instance be determined using a self-learning neural network.

Figure 8:
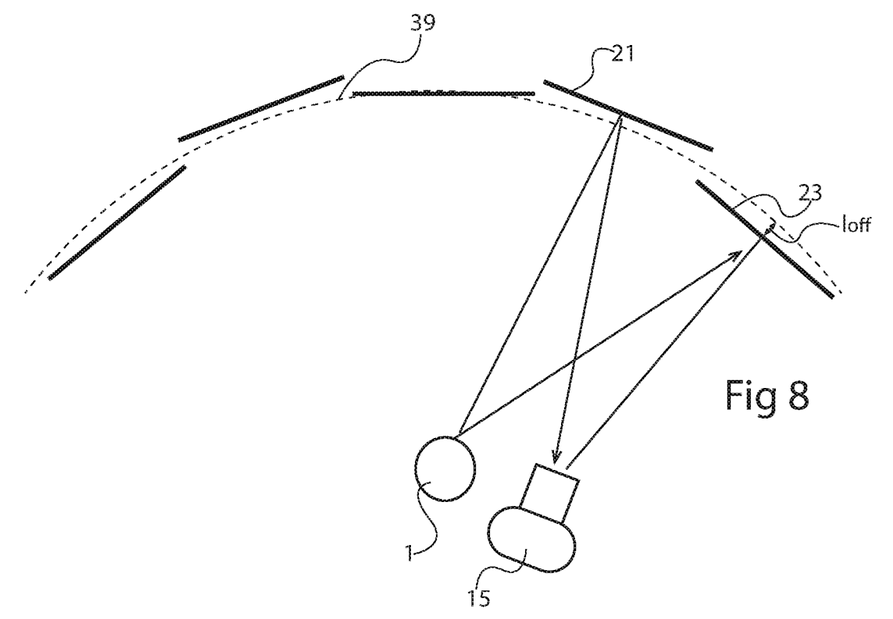
FIG. 8 illustrates offsetting of mirrors to allow a more shallow camera focus depth.

FIG. 8 schematically illustrates a cross section through an example of a mirror support. As illustrated, the mirrors may generally be set up on a spherical curvature 39. The mirrors may however optionally be offset from this curvature, towards or away from the acquisition space, in the direction of the mirror's normal vector 41 a certain length $l_{off}$. By offsetting the mirrors differently, it is made more likely that some of the mirrors will be inside the focus depth of the camera even if this focus depth is small, as different light paths will have slightly different lengths. This allows the use of a wider camera aperture which provides for quicker image rendering. Typically, the light path difference could be about 10% of the cameras focus depth, or about 2% of the shortest optical length between the camera and the eye, although a difference exceeding 1% will provide a substantial effect in many cases.

Figure 9:
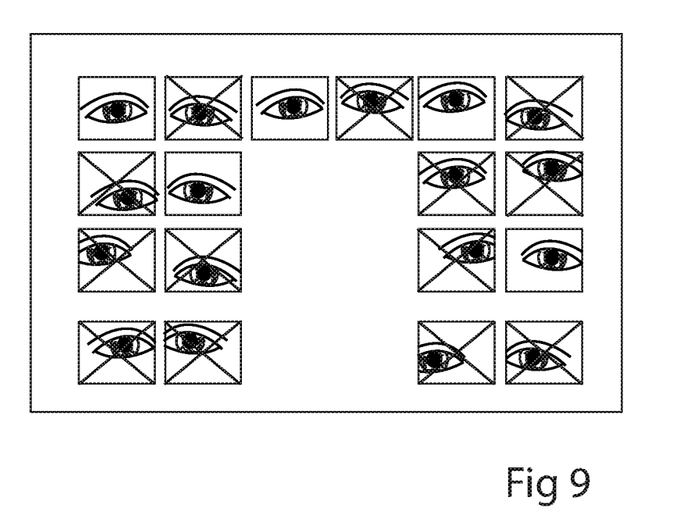
FIG. 9 illustrates post-processing of the image of FIG. 7.

FIG. 9 shows the image of FIG. 7 where a number of subimages have been disregarded for instance for being out of focus, having too great gaze angles, having important features obscured, or providing false information, for instance a double pupil as provided by thick glasses at al substantial angle. Post-processing of the image to provide an eye metric can therefore be carried out only on a small number of subimages, which also provides improved processing speed. In the illustrated case, four subimages, corresponding to four mirrors, two of the right eye and two of the left, are kept for this purpose (other subimages crossed out in the drawing). This may change over time, for instance a few moments later e.g. two subimages corresponding to two other mirrors may be used, for instance if the user has moved his head or changes his gaze angle.

Figure 10:
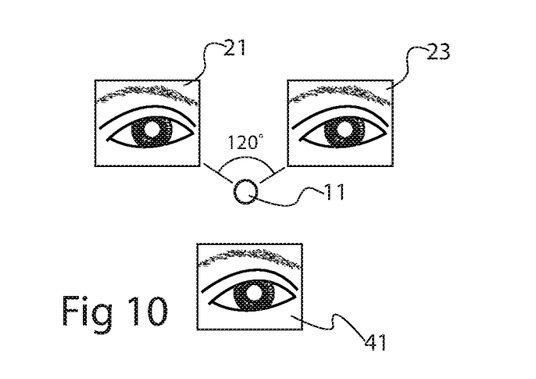
FIG. 10 illustrates a front view of a mirror and light source setup for autorefraction measurements.

FIG. 10 illustrates a front view of a mirror and light source setup for autorefraction measurements. In the figure, three mirrors 21, 23, 41 are viewed as seen from the camera. A light source 11 is located so that the angles between light source and the camera as seen from the eye via the three mirrors 21, 23, 41 is minimized e.g. less than 6°, such that a bright pupil image, cf. FIG. 2, will be produced in each mirror 21, 23, 41, as captured by the camera. With this configuration, differences in the features of the three pictured bright pupils, i.e. the retinas, can be used to determine the eye's refractive errors, both spherical and cylindrical errors. This can be achieved with one single image captured by the camera and comprising the subimages provided by the mirrors. As illustrated, the mirrors may be located at about the same distance from the eye, radially offset from the light source 11 to pupil axis in 120° separation. More mirrors, e.g. six mirrors with 60° separation around the light axis could also be used.

The light source 11' could also be located close to or in front of the camera lens as illustrated in FIG. 5. Returning to FIG. 10, such a light source may provide a light flow towards one or more mirrors. More than one light source may be provided. If arranged in front of the camera lens, it should be avoided that the light source occludes the mirrors or provide light directly into the camera.

The general concept of the present disclosure could also be in connection with wearable configurations. For instance so called virtual reality, VR, glasses could be provided with eye tracking functionalities.

In a simple form, such VR glasses could be accomplished by a head mounted screen with some optics for each eye. For instance, a large screen smartphone can be positioned in front of a users eyes, and a convex lens for each eye can be used to allow the user to watch the screen from short distance. Position sensors in the smartphone can be used to detect the user's head movements and e.g. to change displayed content as a result, in order to e.g. provide a virtual reality effect. In the present disclosure, eye tracking can enhance, for instance, such an effect.

Figure 11:
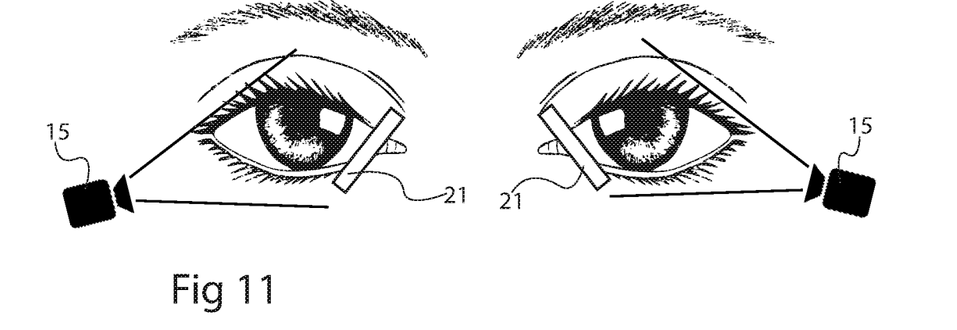
FIG. 11 illustrates a first example of a wearable eye metric acquisition arrangement.

FIG. 11 schematically illustrates a first example of a wearable eye metric acquisition arrangement. This example provides a similar setup as in FIG. 3 for each eye. One camera 15 for each eye captures one direct image of the eye, and one image of the eye via a mirror 21 viewing the eye from another direction. This can be used to provide eye tracking information as previously discussed.

Figure 12:
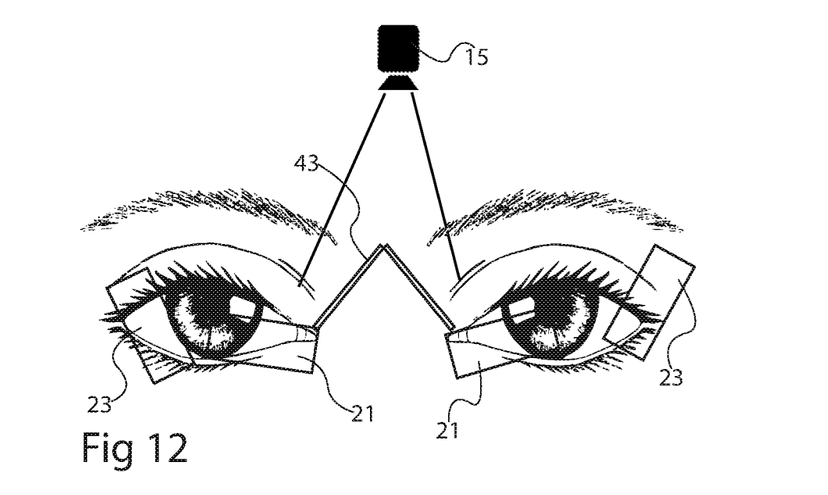
FIG. 12 illustrates a second example of a wearable eye metric acquisition arrangement.

FIG. 12 illustrates a second example of a wearable eye metric acquisition arrangement. In this example, a single camera 15 provides two images each of both eyes of a user. A splitting mirror 41 divides the camera's view into two halves, each producing different images of an eye via a first 21 and a second 23 mirror.

The mirrors 21, 23 used in FIGS. 11 and 12 may be hot mirrors, such that they obstruct the users vision only to a little extent.

The invention has mainly been described with reference to a few embodiments. However, as is readily appreciated by a person skilled in the art, other embodiments than the ones disclosed above are equally possible within the scope of the invention, as defined by the appended patent claims.

The invention claimed is:

1. A device for acquiring a metric of an eye located in an acquisition space, the device comprising:
at least one light source configured to emit light towards the acquisition space,
a camera configured to receive light from the acquisition space to generate image data, and
an analyzing unit configured to extract at least one metric from the image data,
wherein the camera is configured to receive light from the acquisition space via at least first and second light paths simultaneously, wherein the first and second light paths are asymmetrically angled relative to one another with respect to an optical axis of the camera, and
wherein the light received by the camera via the first light path is received via a first mirror, while the light received by the camera via the second light path is received directly from the acquisition space, such that the camera receives light from an overlapping portion of the acquisition space via the first and second light paths, and such that the camera receives at least two different representations of the eye, at the same time.

2. The device according to claim 1, wherein the first and second light paths have a length difference exceeding 1% of the shortest optical path between the eye and the camera.

3. The device according to claim 1, wherein the camera is configured to receive light from a plurality of mirrors, each providing a separate light path between the acquisition space and the camera, the camera being configured to picture an area of the acquisition space that overlaps with an area of another mirror.

4. The device according to claim 3, wherein the plurality of mirrors is disposed on a concave surface facing the acquisition space.

5. The device according to claim 1, wherein a normal of the first mirror and the optical axis of the camera are at an angle of less than 15° relative to one another.

6. The device according to claim 1, wherein the analyzing unit is configured to determine a glint to pupil distance to determine a user's eye gaze angle.

7. The device according to claim 1, wherein the analyzing unit is configured to determine a user's eye gaze angle by carrying out an analysis based on the at least two representations of the eye.

8. The device according to claim 1, wherein the analyzing unit is configured to record images of a user's retina to determine an eye's refractive error.

9. The device according to claim 1, wherein the analyzing unit is configured to determine an iris angular feature to determine a user's eye optical torsion.

10. The device according to claim 1, wherein at least one dichroic filter mirror is located between the acquisition space and the first mirror.

11. The device according to claim 10, wherein first and second dichroic filter mirrors are located in optical paths between the camera and first and second portions of the acquisition space configured for the eye and a second eye, respectively.

12. The device according to claim 1, wherein the at least one light source is configured to produce infrared light.

13. The device according to claim 1, wherein the first and second light paths are of different lengths.

14. The device according to claim 1, wherein the analyzing unit is configured to extract the at least one metric from the image data based on only a subset of the representations of the eye.

15. A method for acquiring a metric of an eye located in an acquisition space, the method comprising:
receiving, via a camera, light from the acquisition space, wherein at least one light source emits light towards the acquisition space;
generating image data; and
analyzing the image data to extract at least one metric therefrom,
wherein the camera is configured to receive light from the acquisition space via at least first and second light paths simultaneously, wherein the first and second light paths are asymmetrically angled relative to one another with respect to an optical axis of the camera, and
wherein the light received by the camera via the first light path is received via a first mirror, while the light received by the camera via the second light path is received directly from the acquisition space, such that the camera receives light from an overlapping portion of the acquisition space via the first and second light paths, and such that the camera receives at least two different representations of the eye, at the same time.

16. The method according to claim 15, further comprising carrying out an analysis based on the at least two representations of the eye to determine a user's eye gaze angle.

\* \* \* \* \*